United States Patent [19]

Pierce

[11] Patent Number: 4,901,372
[45] Date of Patent: Feb. 20, 1990

[54] BARRIER SURGICAL GLOVE

[76] Inventor: William S. Pierce, 1201 Saradana Rd., Harrisburg, Pa. 17112

[21] Appl. No.: 248,827

[22] Filed: Sep. 23, 1988

[51] Int. Cl.$^4$ .............................................. A41D 19/00
[52] U.S. Cl. ......................................... 2/167; 2/161 R; 2/168; 2/21
[58] Field of Search .................. 2/161 R, 167, 168, 21

[56] References Cited

U.S. PATENT DOCUMENTS

| 2,324,735 | 7/1943 | Spanel | 2/168 X |
|---|---|---|---|
| 2,635,240 | 4/1953 | Tausch | 2/168 X |
| 3,094,704 | 6/1963 | Abildgaard | 2/168 X |
| 3,173,150 | 3/1965 | Mohler | 2/167 |
| 3,633,216 | 1/1972 | Schonhaltz | 2/168 |
| 4,270,228 | 6/1981 | Gaiser | 2/158 |
| 4,371,988 | 2/1983 | Berend | 2/167 |
| 4,430,759 | 2/1984 | Jackrel | 2/159 |
| 4,515,851 | 5/1985 | Johnson | 428/246 |
| 4,589,940 | 5/1986 | Johnson | 156/78 |
| 4,696,065 | 9/1987 | Elenteny | 2/168 |
| 4,742,578 | 5/1988 | Seid | 2/25 |
| 4,751,749 | 6/1988 | Cowhey | 2/167 X |
| 4,771,482 | 9/1988 | Shlenker | 2/168 X |

FOREIGN PATENT DOCUMENTS 1154377 7/1956 France ................................... 2/167

OTHER PUBLICATIONS

MAGID Glove, Clothing and Safety Equip. Catalog for Industry Catalog No. 1284, 1985.
New Scientist, Jan. 14, 1988, No. 1595, photograph p. 32.
Nature, vol. 335, No. 6185, Sep. 1, 1988, pp. 19.

Primary Examiner—Werner H. Schroeder
Assistant Examiner—Sara M. Current
Attorney, Agent, or Firm—Thomas Hooker

[57] ABSTRACT

A barrier glove cot or hand covering for protecting surgeons and health care workers includes an integral tri-laminar construction with continuous inner and outer barrier layers and a central foam layer.

23 Claims, 1 Drawing Sheet

BARRIER SURGICAL GLOVE

BACKGROUND OF THE INVENTION

The invention relates to a barrier hand covering, typically a glove or cot for protecting health care workers from patient contamination without sacrificing tactility.

BACKGROUND DESCRIPTION OF PRIOR ART

Single layer surgical gloves, commonly made from latex rubber or vinyl plastic, have been long used by surgeons and health care workers to protect patients from bacteria inevitably present on the worker's hands. The gloves also protect the worker from contamination from the patient. However, these gloves can be easily punctured by suture needles, hypodermic needles and other surgical or medical instruments thereby risking contamination, particularly contamination of the worker by bacterial and viral diseases carried by the patient. These diseases include staphylococcus, hepatitis and the deadly acquired immune deficiency syndrome (AIDS).

It has now been discovered that new single layer surgical gloves often have perforations large enough to permit migration of viruses through the glove. These perforations can allow viruses, including the AIDS virus, to reach the skin of the health care worker. This means that there is a risk that a surgeon or health care worker wearing single layer gloves may contract serious and life threatening diseases even though the gloves appear to be perfect.

Surgeons performing delicate suturing operations are particularly subject to glove puncture by small curved suture needles. The risk of puncture is increased when the procedure is lengthy in duration or performed in an inaccessible surgical field. For instance, there is an increased likelihood of glove puncture during gynecology and cardiac surgery and resultant increased risk of surgeon infection.

In an attempt to reduce the risk of needle puncture surgeons wear two conventional gloves on each hand. This approach is not totally successful because double thickness gloves are still easily punctured and the risk of infection remains. Double gloving also reduces the tactical sensation felt through the two relatively movable glove layers. Thicker single layer gloves made of latex or vinyl plastic have the same disadvantages.

SUMMARY OF THE INVENTION

The invention is directed to a hand covering, typically a barrier surgical glove or finger cot, having a flexible and puncture-resistant tri-laminar construction. The construction includes a continuous impervious inner layer, a continuous impervious outer layer and a continuous central foam layer joined to one or both of the inner and outer layers. The three layers are flexible and conform to the hand of the wearer while transmitting tactile sensations to the wearer.

The tri-laminar construction provides improved barrier resistance to needle sticks or penetration by surgical instruments. The flexible inner and outer layers are barriers against bacterial and viral infection. The foam central layer also serves as a barrier. This construction has an additional advantage that in the event of needle puncture viral or bacterial contamination cannot spread along a joined interface between two layers. After a needle puncture of the foam layer and withdrawal of the needle the resilient foam closes the puncture path and resists subsequent contamination along the puncture path.

Other objects and features of the invention will become apparent as the description proceeds, especially when taken in conjunction with the accompanying drawings illustrating the invention, of which there is one sheet and three examples.

DETAILED DESCRIPTION OF THE EMBODIMENTS

Figure 1:
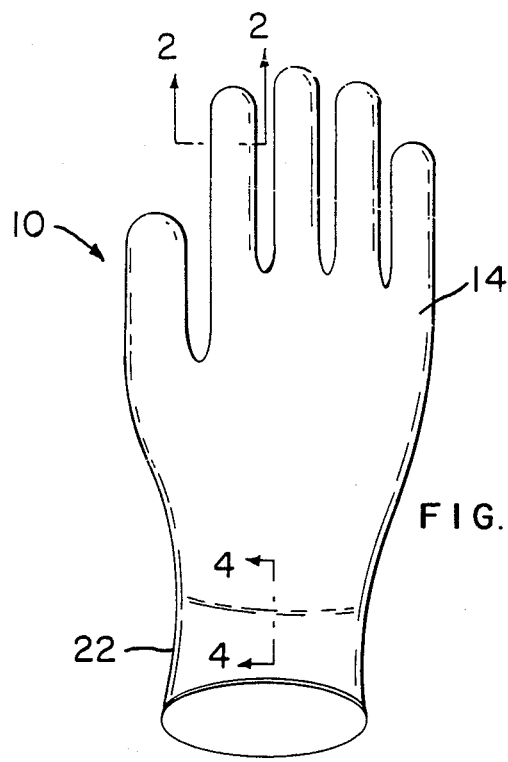
FIG. 1 is a view of a surgical glove according to the invention.
Figure 2:
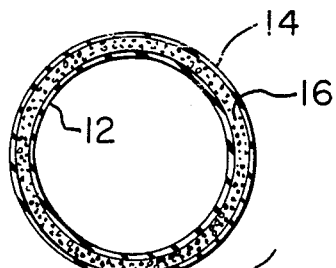
FIG. 2 is a sectional view taken along line 2—2 of FIG. 1.
Figure 3:
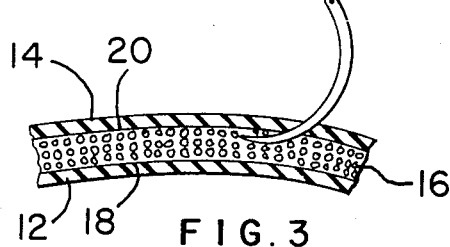
FIG. 3 is an enlarged view of portion of FIG. 2 showing a partial puncture by a suture needle.
Figure 4:
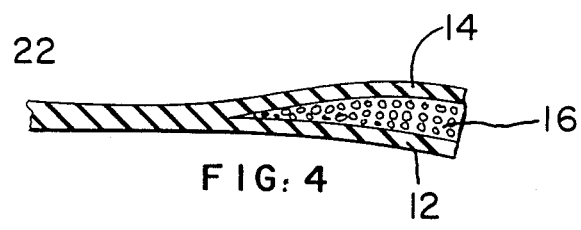
FIG. 4 is a sectional view taken along line 4—4 of FIG. 1.

FIGS. 1 through 4 relate to a barrier surgical glove 10 having a tri-laminar construction in the finger, back and palm areas susceptible to puncture during use. The glove includes continuous inner and outer barrier layers 12 and 14 each generally conforming to the shape of a hand and a continuous foam central layer 16 coextensive with layers 12 and 14 and bonded to the layers 12 and 14 at surface interfaces 18 and 20 to form a tri-laminar glove construction. As shown in FIG. 4, the central layer 16 need not extend into glove cuff 22, although this layer may be coextensive with the entire glove if desired. The glove is resilient and conforms closely to the hand of the wearer like a conventional surgical glove.

The tri-laminar construction protects against puncture and possible resultant contamination both to the surgeon or health car worker wearing the glove and to the patient. It is particularly important to provide this protection during procedures where the gloved hand is exposed to contact by patient tissue and fluids possibly containing dangerous bacteria or viruses.

The inner and outer barrier layers 12 and 14 of glove 10 may be formed from a rubber, such as latex, as illustrated, vinyl, polyurethane or a suitable thin, flexible, resilient and feel-transmitting material capable of stretching sufficiently to permit donning of the glove and collapse on the hand and transmission of a sense of touch through the glove to the wearer.

The foam central layer 16 is made from a strong, soft, flexible, resilient material having a continuous impervious skeleton with a large number of small voids or cells distributed throughout the skeleton. The cells are defined by a dense matrix of walls distributed throughout the layer. This layer may be made of polyurethane foam, polyester foam, latex foam, or other foamed resins or rubbers and the like. The central layer is preferably formed from a skeleton having closed cells so that the layer forms a closed third barrier against contamination.

The tri-laminar construction resists puncture by suture or hypodermic needles. In order to puncture the construction the wedge-shaped needle tip must be driven through the outer layer, each wall in the thickness of the central foam layer and the inner layer. Work is required to puncture, spread and then pass the needle through each individually tough layer and wall along the puncture path. The most common types of needle jabs experienced during surgical and medical procedures are unlikely to occur with a sufficiently high force applied over a sufficiently long period of time to drive the needle through the entire thickness of the tri-laminar construction.

Curved suture needles puncturing the outer glove layer 14 may follow a curved path and bury themselves in the central foam layer without completely penetrating the glove. See FIG. 3. In this case, inner layer 12 maintains the integrity of the glove and prevents contamination. The glove also resists puncture by hypodermic needles and other surgical instruments.

The puncture resistance of glove 1 is particularly important for protecting a surgeon during long procedures where the operative field is limited and cannot be readily observe. Suture needles are small and can be difficult to handle by even the most skilled of practitioners. A likelihood of a needle tip being driven against a glove is always present. The tri-laminar construction reduces the risk of a resultant puncture through the glove.

Figure 5:
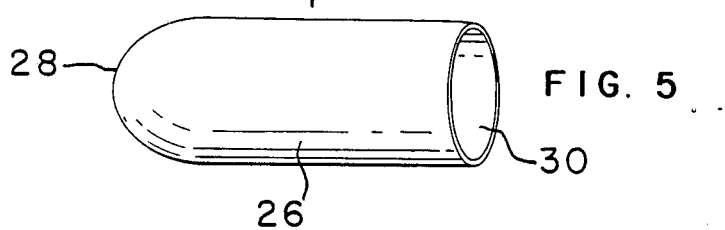
FIG. 5 is a view of a finger cot according to the invention.
Figure 6:
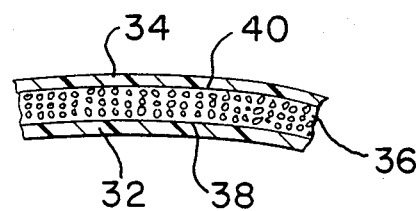
FIG. 6 is a section a view taken through the thickness of the cot of FIG. 5.

FIGS. 5 and 6 disclose a finger cot 24 according to the invention having a cylindrical body 26, a closed end 28 and an open end 30 permitting fitting of the cot over the finger of the wearer. The cot is similar to one finger of glove 10. The inner and outer barrier layers are bonded to a foam central layer 36 at interfaces 38 and 40 like interfaces 18 and 20. Layer 36 may be identical to layer 16. Cots 24 are used to protect the fingers of health care workers where it is not necessary to protect the full hand.

The tri-laminar constructions of illustrated glove 10 and cot 24 are identical with the exception that rubber barrier layers are used in the glove and plastic barrier layers are used in the cot. These barrier layers are equivalent. Other types of tri-laminar constructions may be used in the gloves and cots. For instance, a glove or cot may have an integral tri-barrier construction with a central flexible and tactical sensation transmitting layer formed from a plastic foam with integral inner and outer skin layers to either side of the central layer formed by surface curing of the material forming the central foam layer. These outer and inner skin layers function like layers 12, 14 and 32, 34 and are integral with the central layer to form a glove or cot with superior puncture resistance and the capability of transmitting tactical sensations to the wearer.

The tri-laminar construction of the glove and cot may have a total thickness ranging from about 0.030 inch to about 0.060 inch. As an example, the glove or cot may have a total thickness of 0.040 inch with the inner and outer layers being 0.10 inch thick and the central foam layer being 0.020 inch thick. A glove or cot of this construction has a thickness about four times greater than the thickness of a conventional single layer surgical glove. Increased thickness of this range does not materially restrict the wearer from carrying out medical and surgical procedures, provided tactility is maintained.

Figure 7:
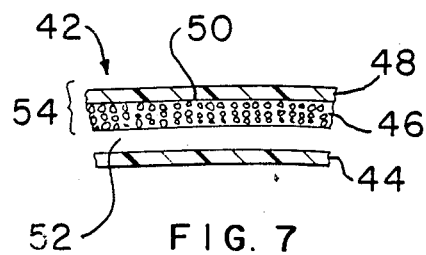
FIG. 7 is a sectional view taken through another example barrier surgical glove.

Another example barrier surgical glove 42, shown in the section in FIG. 7, is similar in shape to glove 10 and includes an inner barrier layer 44, a foam central layer 46 and an outer barrier layer 48. The inner surface of the outer barrier layer is joined to the outer surface of the central layer at interface 50 Layers 44 and 46 are not joined together. In FIG. 7 a space 52 is shown separating the inner layer 44 from a central layer-outer layer assembly 54. The layers 44, 46 and 48 are like the previously described inner, central and outer layers. In glove 42, the inner layer 44 may be a conventional surgical glove which can be donned by the wearer for use independent of assembly 54.

The assembly 54 comprising the central layer 46 and outer layer 48 may be manufactured as a unit in the configuration of a glove. The outer layer may be a skin layer integral with the central foam layer and formed of the same material as the foam layer.

The assembly is donned by a surgeon or health care worker already wearing an inner layer or conventional glove prior to performing a procedure requiring added protection against puncture. It is a simple matter to draw the resilient assembly 54 over the previously donned glove or inner layer 44 to form a barrier surgical glove 42 with the protective tri-laminar construction previously described. After the assembly has been donned it surrounds and resiliently fits on the inner glove to eliminate any space 52 between the inner and central layers, thereby assuring transmission of tactile sensations through the barrier glove to the wearer. Either the assembly only or the assembly and the inner layer 44 may be stripped from the hand of the wearer as required.

A cot assembly may be formed having a central foam layer like layer 46 and an outer barrier layer like layer 48. Cot assemblies of this type may be drawn over the fingers of previously donned inner layer conventional surgical gloves to form tri-laminar barrier surgical cots.

Although the invention has been described with reference to gloves and cots, it extends to all surgical hand coverings using the described barrier construction. Accordingly, while I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A barrier surgical hand covering having a puncture-resistant and tactile sensation transmitting construction, the covering comprising:
   (a) a continuous central foam layer formed of a flexible, resilient and puncture-resistant first material having a dense matrix of spaced walls distributed throughout the layer, said walls defining a skeleton with a large number of closely spaced closed cells distributed throughout the layer; and
   (b) continuous inner and outer flexible, resilient and imperforate contamination barrier layers formed of second and third materials, one barrier layer being joined to one side of the central layer along the surface interface therebetween, said layers forming a tri-laminar construction.

2. A covering as in claim 1 wherein the outer layer comprises An un-foamed skin integrally joined to the central portion.

3. A covering as in claim 2 wherein said first and third materials are polyurethane.

4. A covering as in claim 1 wherein the central layer consists of a plastic resin foam.

5. A covering as in claim 1 wherein the outer barrier layer is integrally joined to the outer surface of the central layer.

6. A covering as in claim 5 wherein the inner barrier layer is integrally joined to the inner surface of the central layer.

7. A surgical glove having construction as in claim 1.

8. A surgical glove as in claim 7 wherein said construction extends around the fingers, palm and back of the glove and has a thickness of from about 0.03 inch to about 0.06 inch.

9. A surgical glove as in claim 7 the central layer has a thickness of about 0.02 inch and each inner and outer layer has a thickness of about 0.01 inch.

10. A finger cot having a construction as in claim 1.

11. A covering as in claim 1 wherein the central layer is thicker than either of the other layers.

12. A covering as in claim 1 wherein the central layer is formed from a polyurethane foam.

13. A barrier surgical glove comprising:
 (a) a continuous inner barrier layer extending around the fingers and across palm of the glove;
 (b) a continuous outer barrier layer extending around the fingers and across palm of the glove outside of the inner layer;
 (c) each of said layers being formed from a flexible, resilient and imperforate barrier material; and
 (d) a continuous central layer extending around the fingers and across palm of the glove between the inner and outer barrier layers and joined to the outer layer along the interface between the layers to prevent contamination migration along the interface, said central layer being formed from flexible, resilient and puncture-resistant foam material having a dense matrix of spaced walls distributed throughout the layer, said walls defining a skeleton with a large number of closely spaced closed cells distributed throughout the skeleton.

14. A glove as in claim 13 having a thickness of from about 0.03 inch to about 0.06 inch.

15. A glove as in claim 13 the central layer is formed from a plastic resin foam.

16. A glove as in claim 13 wherein the central layer is formed from polyurethane foam.

17. A glove as in claim 13 wherein the outer layer is formed from the same material as the central layer and comprises a skin integrally joined to the central layer.

18. A barrier surgical hand covering assembly adapted to be worn on the hand over a single layer surgical glove to form a puncture resistant tri-laminar construction, the assembly comprising a resilient continuous outer barrier layer having a configuration conforming to an adjacent part of the glove; and a continuous central layer extending around the interior of the outer barrier layer and bonded to the outer barrier along the surface interface between the layers to prevent contamination migrating along the interface, said central layer being formed from a flexible, resilient puncture-resistant foam material having a dense matrix of spaced walls distributed throughout such layer, said walls defining a skeleton with a large number of closely spaced closed cells distributed throughout the skeleton.

19. An assembly as in claim 18 wherein said layers are formed from foamed and unfoamed portions of the same material and wherein said outer barrier layer comprises a skin integrally joined to and formed with the central foam layer.

20. An assembly as in claim 18 having the shape of a glove.

21. An assembly as in claim 18 having the shape of a finger cot.

22. A barrier surgical hand covering comprising:
 (a) A continuous inner barrier layer adapted to extend over a portion of a hand;
 (b) A continuous outer barrier layer overlying the inner layer;
 (c) Each of said layers being formed from a flexible, resilient and imperforate barrier material; and
 (d) A continuous central layer located between said inner and outer layers and joined to one of said layers along an interface therebetween to prevent contamination migration along the interface, said central layer being formed from flexible, resilient and puncture-resistant closed cell foam means.

23. A hand covering as in claim 22 wherein said central layer comprises a continuous dense matrix of spaced walls distributed throughout the layer and defining said closed cells.

* * * * *